United States Patent [19]

Paul et al.

[11] Patent Number: 5,607,459
[45] Date of Patent: Mar. 4, 1997

[54] IMPLANTABLE CARDIAC STIMULATION DEVICE WITH TIME-OF-DAY SELECTABLE WARNING SYSTEM

[75] Inventors: Patrick J. Paul; David Prutchi, both of Lake Jackson, Tex.

[73] Assignee: Intermedics, Inc., Angleton, Tex.

[21] Appl. No.: 613,127

[22] Filed: Mar. 8, 1996

Related U.S. Application Data

[63] Continuation-in-part of Ser. No. 549,050, Oct. 27, 1995.
[51] Int. Cl.$^6$ ..................................................... A61N 1/37
[52] U.S. Cl. ..................................................... 607/29
[58] Field of Search .................................... 607/17, 18, 19, 607/20, 27, 29

[56] References Cited

U.S. PATENT DOCUMENTS 5,143,065  9/1992  Adkins et al. ........................ 607/19

Primary Examiner—William E. Kamm
Assistant Examiner—Scott M. Getzow
Attorney, Agent, or Firm—John R. Merkling

[57] ABSTRACT

A cardiac stimulator including a patient warning apparatus, having a real time-clock for delaying delivery of a warning stimulus until a preselected time of day. The time of day may be selected dynamically with respect to detected patterns of patient activity. The stimulator can adjust the time for delivery of patient warning based on the detected circadian rhythm of the patient. In one embodiment, the cardiac stimulator is an implantable pacemaker or defibrillator or combination which can also be programmed to automatically alter the peak voltage of its output stimulus, in particular, to increase the peak voltage of the output stimulus whenever a condition exists requiring patient notification or warning. A stimulus generator in the stimulator can delivers electrical current to the electrically conductive suture point or warning electrode at a preselected voltage level. A sensor for detecting patient reaction to a warning stimulus may be an accelerometer or motion/vibration transducer or other sensor capable of detecting a reaction to a warning stimulus. The level of the stimulus directed to the patient's skeletal muscle is regulated until a preselected magnitude of reaction has been achieved. The reaction is also maintained below a pre-selected maximum to avoid discomfort to the patient.

28 Claims, 3 Drawing Sheets

IMPLANTABLE CARDIAC STIMULATION DEVICE WITH TIME-OF-DAY SELECTABLE WARNING SYSTEM

This is a continuation-in-part of U.S. patent application Ser. No. 08/549,050, filed Oct. 27, 1995, pending.

FIELD OF OUR INVENTION

Our invention relates to implantable medical devices and particularly to cardiac pacemakers and other cardiac stimulators which monitor the operation of the heart and stimulate the heart tissue as required to maintain the proper operation of the heart, including implantable cardioverters and defibrillators. In particular, our invention relates to an implantable cardiac stimulating system with the capability of alerting or warning a patient of certain conditions or situations, including, without limitation, battery depletion, lead malfunction, or the eminent delivery of therapy.

BACKGROUND OF OUR INVENTION

Implantable medical devices have been developed to treat a wide variety of conditions. Such devices may deliver controlled quantities of drugs, stimulate nerves, or control muscles. In particular, devices have been developed to treat the diseased or malfunctioning heart.

It has long been known that the heart muscle provides its pumping function in response to electrical events which occur within the atrium and ventricle of the heart. Conductive tissue connects the atrium and the ventricle and provides a path for electrical signals between the two areas. In a normal heart, a natural atrial event spontaneously occurs in the atrium and a corresponding ventricular event occurs later in the ventricle. Synchronized electrical events occurring naturally in the atrium and ventricle cause the heart muscle to rhythmically expand and contract and thereby pump blood throughout the body.

In a diseased heart, atrial and ventricular events may not naturally occur in the required synchronized manner and the pumping action of the heart is therefore irregular and ineffective to provide the required circulation of blood. The required synchronized activity of such diseased hearts can be maintained by an implanted cardiac pacemaker which applies synchronized stimulating pulses to either the atrium or ventricle or both.

A diseased heart may also beat unusually quickly, a condition known as tachycardia, or may lapse into a rapid, disorganized quivering known as fibrillation. The former condition is undesirable; the latter condition may be fatal. To correct these conditions, implantable cardioverters and defibrillators have been proposed. Like the related cardiac pacemaker, these devices monitor the electrical condition of the heart and provide a corrective electrical therapy to correct the improper heart function. The three functions of pacing, cardioverting and defibrillating, or any of them, may be incorporated into a single device, generically referred to as an implantable cardiac stimulator.

Cardiac stimulators are battery powered and, consequently, have a finite life before battery depletion may be expected. In addition to the battery, other components of the cardiac stimulation system may fail, such as leads, electrodes, or other system components. As an example of another type of change, the sensitivity of a patient's heart to electrical stimulation may change over time, altering the so-called threshold level for electrical stimulation. Such change of condition requires adaptation of the therapy delivered by the implantable cardiac stimulator, either automatically or by intervention by the attending physician. In any of these situations, or others, it may be deemed desirable to alert the patient to a changed condition so that action may be taken. For example, a pacemaker may detect the approaching end-of-life of its battery, in a known manner. It is desirable to alert the patient to this condition. Moreover, in the case of implantable defibrillators, delivery of therapy can be traumatic. It is sometimes deemed important to alert the patient to the prospect of eminent delivery of therapy.

Cardiac stimulators which alert or warn the patient of such conditions are known in the art. For example, such a device is described by Dutcher, et al. in U.S. Pat. No. 4,140,131. In the device described by Dutcher, et al., a device-controlled switch is activated to enable a specialized electrode adjacent the pacemaker to stimulate the patient's muscles to twitch. The nature of the electrode is not described in detail, but Ferek-Petrick, in U.S. Pat. No. 5,076,272, described the electrode of Dutcher, et al., as an auxiliary electrode surrounded by the indifferent electrode and fixed on the pacemaker can. In contrast, Ferek-Petrick, in U.S. Pat. No. 5,076,272, describes a cardiac stimulator with patient warning with an electrode affixed to the header of the stimulator. Another electrode is described in our U.S. patent application Ser. No. 08/426,949, filed Apr. 21, 1995, also assigned to Intermedics, Inc.

In yet another commonly assigned U.S. patent application Ser. No. 08,532,929, filed Sep. 22, 1995, a suture point or hole, commonly provided on a header of a stimulator, is modified to provide an electrical connection. An electrically conductive suture can then be used to secure the stimulator and to provide a connection for stimulus of the skeletal muscles of the patient to produce an effective twitch. The disclosure of that application is incorporated herein by reference.

In any of these configurations, the desired result is a noticeable reaction in the skeletal muscles of the patient sufficiently strong to alert the patient, but not painful. Patients differ from one another, however, and stimulation sufficient to cause a satisfactory reaction in one patient may be either insufficient or excessive in another. Moreover, the contact between an implanted device and surrounding tissue may change over time, with the result that a stimulation of a particular magnitude may have a different and unpredictable result. Also, the sensitivity of skeletal muscle to stimulation may change. U.S. patent application Ser. No. 08/549,050 describes a cardiac stimulator with a patient warning apparatus which automatically adjusts the magnitude of applied stimulus to achieve a desired level of reaction.

Although the level of reaction of the patient to a stimulus is important in assuring that the patient will actually receive a warning of changed condition, we believe that a patient will be more likely to perceive and appreciate a warning stimulation if that stimulation is delivered at a preselected time of day and particularly at a time when the patient is not likely to be sleeping or otherwise less likely to perceive a stimulus. It is the principle object of our invention, therefore, to provide a cardiac stimulator with patient warning apparatus which will warn the patient at a preselected time of day, rather than merely upon the occurrence of the preselected condition. It is also an object of our invention to provide such a cardiac stimulator which can dynamically adjust such a real time warning period to adapt for the circadian rhythm of the patient, or changes in wake-sleep patterns of the patient. It is also an object of our invention to provide a cardiac stimulator which distinguishes between conditions for which a warning must be given immediately upon the occurrence of the condition, and other conditions for which a warning can be postponed to a preselected time of day.

SUMMARY OF OUR INVENTION

In view of the foregoing, we have invented an implantable medical device including a patient warning apparatus, having a real time-clock for delaying delivery of a warning stimulus until a preselected time of day. Moreover, the time of day may be selected dynamically with respect to detected patterns of patient activity. The stimulator can adjust the time for delivery of patient warning based on the detected circadian rhythm of the patient. Detection of a patient's circadian rhythm is more particularly described in U.S. Pat. No. 4,922,930. In our preferred embodiment, the implantable medical device is a cardiac stimulator including an implantable pacemaker or defibrillator or combination which can be programmed.

In one embodiment, the cardiac stimulator is an implantable pacemaker or defibrillator or combination which can also be programmed to automatically alter the peak voltage of its output stimulus, in particular, to increase the peak voltage of the output stimulus whenever a condition exists requiring patient notification or warning. A stimulus generator in the stimulator can delivers electrical current to the electrically conductive suture point or warning electrode at a preselected voltage level. A sensor for detecting patient reaction to a warning stimulus may be an accelerometer or motion/vibration transducer or other sensor capable of detecting a reaction to a warning stimulus. Means for adjusting the level of the stimulus directed to the patient's skeletal muscle regulate the stimulus until a pre-selected magnitude of reaction has been achieved. The reaction is also maintained below a pre-selected maximum to avoid discomfort to the patient.

With the foregoing in mind, we will now describe the preferred embodiment of our invention with respect to the accompanying drawings.

DETAILED DESCRIPTION OF OUR PREFERRED EMBODIMENT

Figure 1:
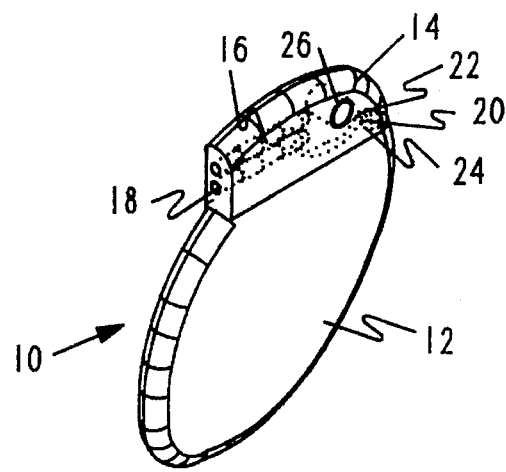
FIG. 1 is a perspective drawing of a cardiac stimulator with a patient warning system.

FIG. 1 is a perspective drawing of a cardiac stimulator, generally designated 10, according to our invention. We have illustrated our invention in connection with a dual chamber pacemaker, but our invention is equally applicable with other implantable cardiac stimulators such as cardioverters and defibrillators, as are known in the art. The cardiac stimulator 10 comprises a hermetically sealed case or can 12 which, in a known fashion, contains batteries and electrical circuitry. A header 14, attached to the can 12, has two sockets 16, 18 to which leads can be mechanically and electrically connected. Leads are commonly used to place the cardiac stimulator 10 in electrical communication with the heart or other body tissues. Electrical conductors 22, 24 provide an electrical connection between the sockets 16, 18 and the circuitry inside the can 12 through a feed-through 20. In the illustrated dual chamber pacemaker, one channel of stimulation circuitry connected to socket 18 would usually be used to sense and stimulate the ventricle of the heart, while another channel of stimulation circuitry connected to socket 16 would usually be used to sense and stimulate the atrium of the heart. An electrical stimulus is also used for warning the patient of certain conditions, such as low battery power, through a warning electrode, such as an electrically conductive suture point or hole 26 or other type of electrode. A dedicated stimulation generator is connected to the conductive suture point or warning electrode, as more fully explained below. A wide range of patient warning electrodes, as are known in the art, may be employed with our invention. Moreover, although our preferred embodiment comprises a cardiac stimulator, other implantable medical devices could also incorporate our invention. Such devices could include drug delivery systems, nerve stimulators or muscle stimulators which produce a therapy for treatment of a patient. Such medical devices usually include means for delivering the therapy to a selected location within the patient. For example, a drug delivery system might employ a catheter, while a nerve stimulator might employ a lead and electrode, similar to lead and electrode described herein in connection with a cardiac stimulator.

Figure 2:
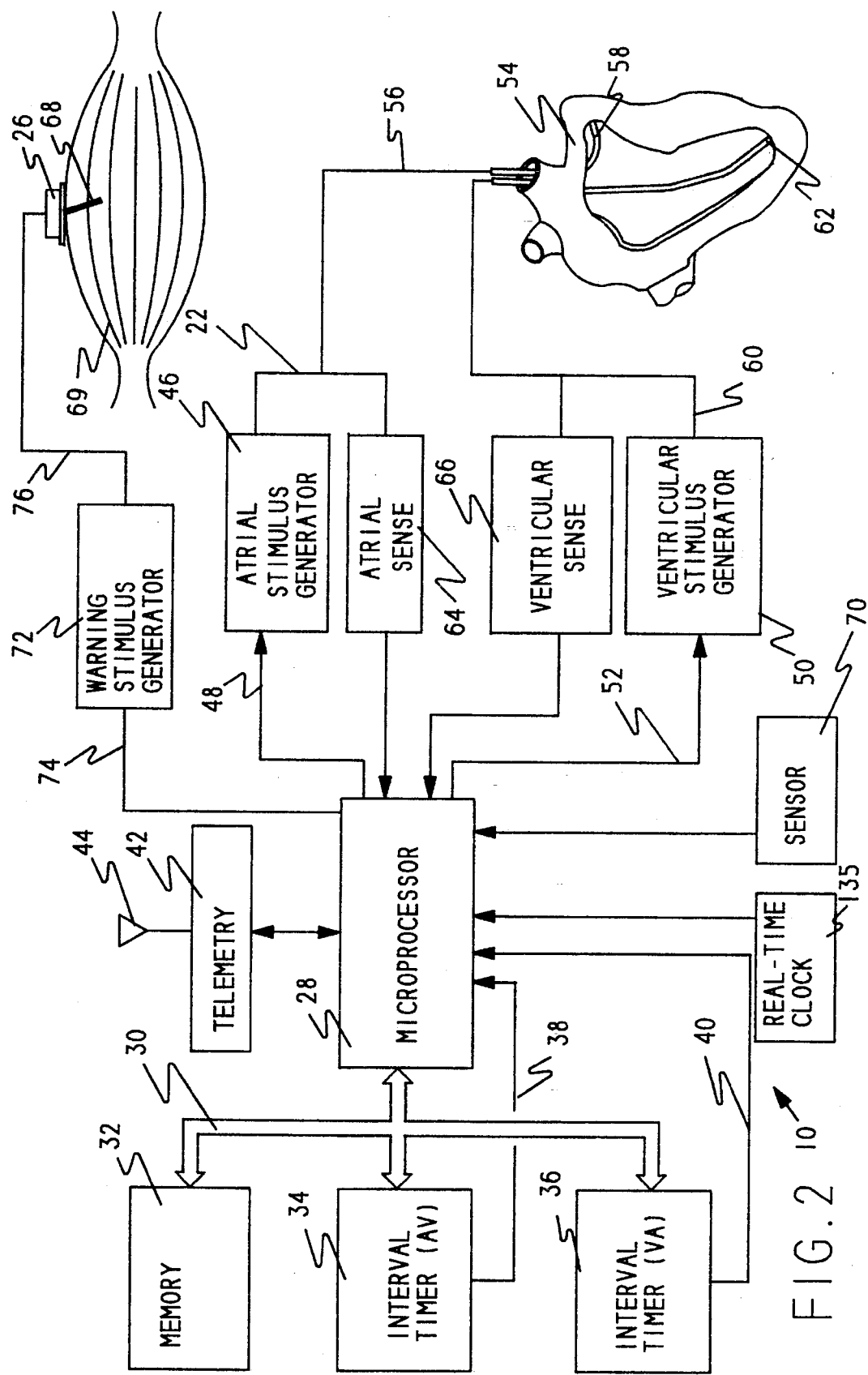
FIG. 2 is a block diagram of a cardiac stimulation system.

As shown in FIG. 2, in the can 12 of the cardiac stimulator 10, a microprocessor 28 preferably provides control and computational facilities. It will be appreciated that other forms of circuitry, such as analog or discrete digital circuitry, can be used in place of the microprocessor 28. However, a microprocessor is preferred for its miniature size and flexibility, both of which are of critical importance for the implantable systems in which it is envisioned our invention will find use. More particularly, a cardiac stimulator having a microprocessor can usually be re-programmed to utilize our invention without additional structural changes, with the exception of the provision of a real time clock and, optionally, a sensor such as an accelerometer. A particularly energy efficient microprocessor which is designed specifically for use in pacemakers is fully described in Gordon, et al, U.S. Pat. No. 4,404,972, which is assigned to the assignee of our invention. The disclosure thereof is incorporated herein by reference.

The microprocessor 28 has input/output ports connected in a conventional manner via a bi-directional bus 30 to memory 32, an AV interval timer 34, and a VA pacing interval timer 36. In addition, the AV interval timer 34 and VA interval timer 36 each has an output connected individually to a corresponding input port of the microprocessor 28 by lines 38 and 40 respectively. Memory 32 preferably includes both ROM and RAM. The microprocessor 28 may also contain additional ROM and RAM as described in Gordon, et al., above. Generally, the pacemaker operating routine is stored in ROM or EPROM memory. RAM stores various programmable parameters such as executable code and variables used in conjunction with the pacemaker operation. The AV and VA interval timers 34, 36 may be external to the microprocessor 28, as illustrated, or internal thereto, as described in Gordon, et al., above. The timers 34, 38 are conventional up or down counters of a type initially loaded with a count value and count up to or down from the value and output a roll-over bit on completing the programmed count.

The microprocessor 28 preferably has an input/output port connected to a telemetry interface 42. The implanted cardiac stimulator 10 is thus able to receive pacing, rate control, or other parameters from an external programmer through an antenna 44 and to send data to an external receiver if desired. Many suitable telemetry systems are known to those skilled in the art. One such system and coding arrangement is described in Calfee, et al. U.S. Pat. No. 4,539,992 which is also assigned to the assignee of our invention. That description is incorporated therein by reference.

Microprocessor output ports are connected to the input of an atrial stimulus pulse generator 46 by a control line 48. Similarly, a ventricular stimulus generator 50 is connected to the microprocessor by a control line 52. In our preferred embodiment, a dedicated warning stimulus generator 72 is connected to the microprocessor by a control line 74. Instead of a dedicated generator 72, a switch controlled by the microprocessor could also be employed to re-direct the output of either the atrial stimulus generator 46 or the ventricular stimulus generator 72 to the warning electrode 26. Alternatively, the output of one of the stimulus generators, for example, the atrial stimulus generator, could be dedicated to producing a patient warning through a lead or electrode connected to excitable tissue. The microprocessor 28 would usually be programmed to act as a single chamber pacemaker and the other channel or stimulus generator would be dedicated to producing warning pulses. Such a configuration is more fully described in U.S. patent application Ser. No. 08/532,261, which is assigned to Intermedics, Inc., and which is incorporated herein by reference.

The microprocessor 28 transmits pulse parameter data, such as pulse amplitude and width, as well as enable/disable and pulse initiation codes to the stimulus generators 46, 50, 72 along their control lines 48, 52, 74 respectively. The atrial stimulus generator 46 is connected to the heart 54 by a first lead 56 with an electrode 58. Similarly, the ventricular stimulus generator 50 is connected to the heart 54 by a second lead 60 with a corresponding electrode 62. The warning pulse generator 72, in contrast, is connected by a conductor 76, which may be internal to the pacemaker 10 or may comprise a lead, to the warning electrode 26 which is in contact with skeletal muscle.

The electrical condition of the heart must also be sensed and that condition must be transmitted to the microprocessor 28. For this purpose, an atrial sense amplifier 64 is connected between the lead 56 and the microprocessor 28. Similarly, a ventricular sense amplifier 66 is connected between the lead 60 and the microprocessor 28. The atrial and ventricular sense amplifiers 64, 66 detect occurrences of P waves and R waves respectively. The cardiac stimulator 10 of our invention is also provided with at least one warning electrode, illustrated as an electrically conductive suture hole or point 26. Two or more suture points could be provided. The suture point 26 is connected to the warning stimulus generator 72 which allows a stimulating pulse to be passed through an electrically conductive suture 68 attached to excitable tissue 69 of the patient. The magnitude of the warning pulse is controlled by the microprocessor, preferably between about 0.2 volts and 8 volts.

The pacemaker 10 is also provided with a sensor 70 sensitive to the reaction of the patient to warning stimulus through the warning electrode. In the illustrated embodiment, the sensor is an accelerometer such as that described by Alt in U.S. Pat. No. 4,926,863. A suitable accelerometer is also described by Leonhardt in U.S. Pat. No. 5,235,237. Preferably, the pacemaker is a rate-responsive pacemaker which responds to changing physiologic needs of the patient by adjusting the pacemaking rate, as described in the '863 patent. Other suitable sensors are also known such as a body vibration or microphone type sensor described by Anderson in U.S. Pat. No. 4,428,378. As described below, the output of the sensor 70 is closely scrutinized by the microprocessor after a warning stimulus to see if the warning stimulus produced the desired physiologic response in the patient.

Figure 3:
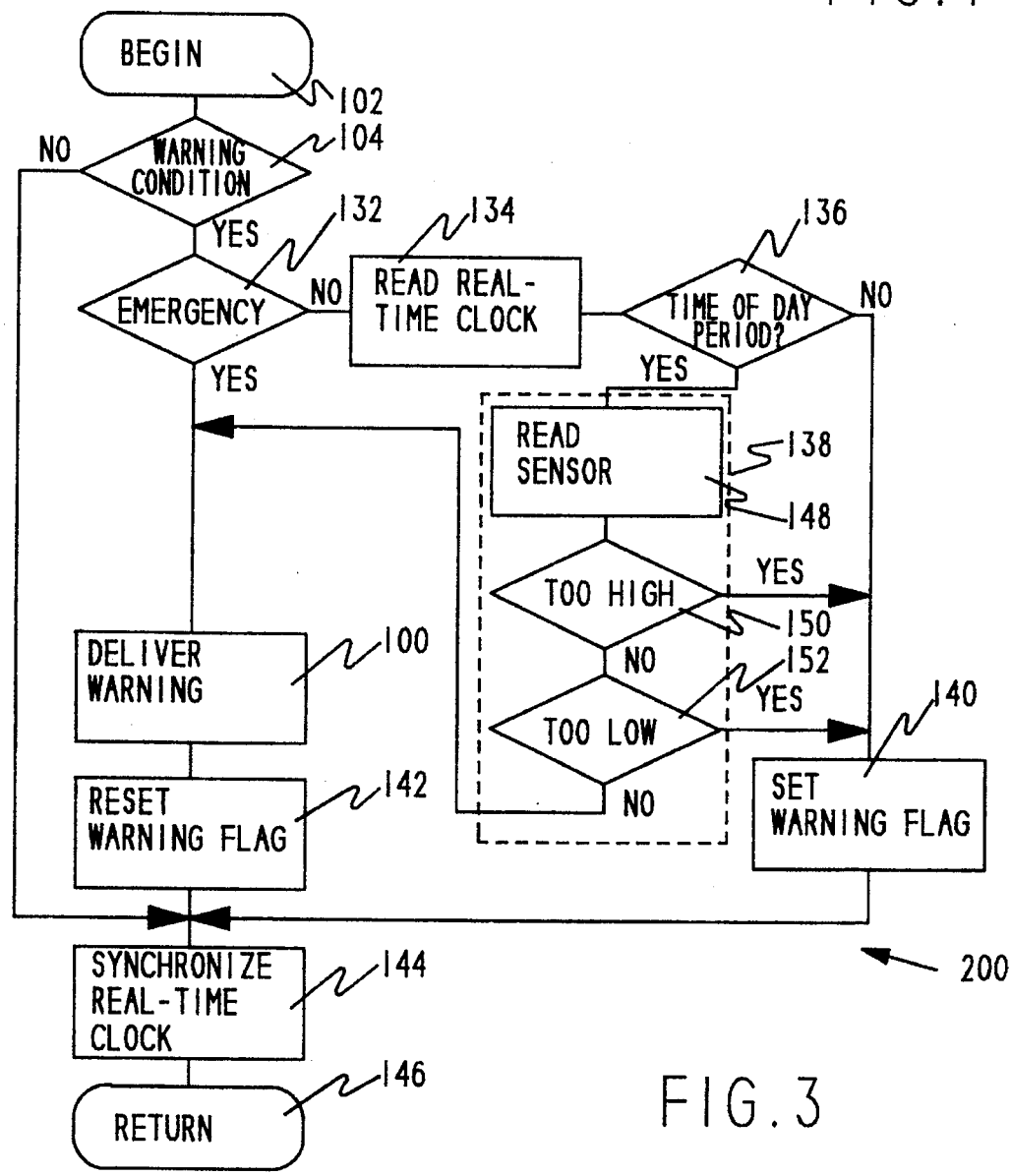
FIG. 3 is a flow chart for a time-of-day delay program to be implemented in the cardiac stimulation system of FIG. 2.
Figure 4:
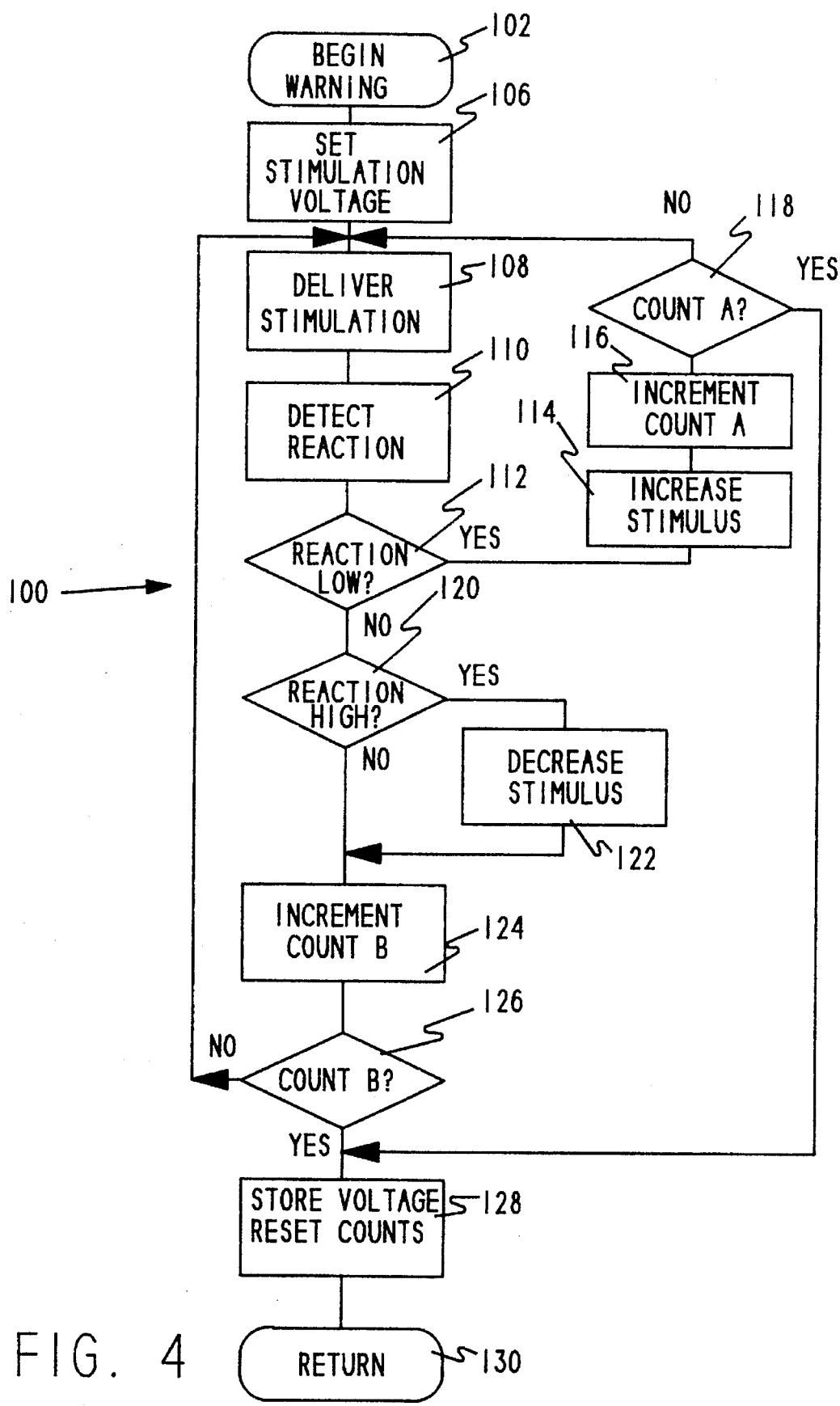
FIG. 4 is a flow chart for a warning delivery sub-routine.

The pacemaker is programmed to produce an electrical stimulation to notify the patient of a condition. In prior art devices such as that disclosed in U.S. Pat. No. 5,076,272, various conditions requiring patient notification or warning have heretofore been identified. In the pacemaker, a warning program, such as that indicated at 200 in FIG. 3 and 100 in FIG. 4, is needed. In addition to other standard pacemaker or cardioverter programming, the warning program 200 would begin 102 and pass to a test 104 to enquiring whether the patient should be notified or not. This program sequence could be a single test controlling a flag, or it might involve multiple tests for different conditions recognized by pacemaker programming and identified in an appropriate manner, such as by setting a software flag. These tests could include battery power or voltage level, failure of the pacing lead, presence of strong electromagnetic noise in the immediate surroundings of the patient, presence of inappropriate tachycardia, or eminence of an impending defibrillation shock or other therapy, among other indicators. If there is no condition existing justifying notification or warning of the patient, no further action need be taken in this segment of the microprocessor programming and the program control can branch around the next steps. If it is desired, however, to notify the patient, the microprocessor tests at 132 to determine if the detected condition is an emergency which requires immediate attempted notification of the patient. Such conditions might include catastrophic failure of the pacing lead, eminence of a impending defibrillation shock, or such other similar indicator. If an emergency condition exists, the microprocessor would immediately implement a deliver warning subroutine 100. The deliver warning subroutine 100 is more fully illustrated in FIG. 4, and will be described in detail hereafter. If the condition is not deemed to constitute an emergency, the microprocessor will read 134 a real time clock 135 to determine if a preselected time of day condition is met. The real time clock 135 produces a 24 hour cyclic timing signal so that it can be determined by the microprocessor if a preselected time period has been achieved, for example, between 3:00 and 3:30 in the afternoon. In the simplest embodiment, the real time clock 135 simply produces a 24-hour cycle so that a selected period within that cycle can be designated by programming to be a warning time during which nonemergency warning conditions would be activated. We contemplate, however, that patients may also travel or move from one time zone to another and that a strict clock could become out of synchrony with real world diurnal cycles. Using detected motions of the patient from the sensor 70, the microprocessor 28 can, at step 144 for example, adjust the real time clock or its starting point to maintain synchrony with the diurnal cycle of the patient. Maintenance of such a cycle is particularly described in U.S. Pat. No. 4,922,930 to Adkins and Baker, the disclosure of which is incorporated herein by reference. By adjusting the real time clock and its starting time, a designated time period can be maintained which corresponds to the patients actual diurnal pattern. Thus, if a half hour window in a mid-afternoon time period were selected and programmed by the physician, the cardiac stimulator could maintain that mid-afternoon window despite changing conditions such as long distance travel.

In addition to setting an absolute time window as described above, the cardiac stimulator could also be programmed to warn the patient during a time window defined by proportion to detected patient patterns. That is, as described in the '930 patent, a particular patient may manifest a changing circadian rhythm or wake-sleep pattern. The patient's usual waking period may become longer or shorter over extended periods. Most people, for example, sleep longer in winter than in summer months, and this pattern can be detected by the cardiac stimulator as described in the '930 patent. As an alternative to a fixed time of day, therefore, it is possible to set a dependent warning period, for example, two hours after the patient's usual time of waking, a period which might notify the patient at a time when it would be possible for the patient to contact the attending physician. Similarly, the warning window or period in which non-emergency warnings would be delivered to the patient could be set as a proportion of a detected period, for example for a half hour period ⅓ of the way through the patient's normal waking period. The object is to designate an appropriate period of time when the patient would most likely be receptive to detecting a warning signal and might also be able to respond in an appropriate manner. The patient would be more likely to perceive the warning because a window would usually be selected when the patient would normally be awake. The patient would also be more likely to correctly identify the warning because a warning stimulus during the preselected time window would be expected.

If the microprocessor determines at 136 that the time of day window is appropriate, control would be passed to an activity subroutine 138 or directly to the deliver warning subroutine 100. If the time of day window has not been reached, a flag would be set 140 indicating that a warning should be delivered and the program would continue to cycle through its other tests and programming until the time of day window was reached. After delivering the warning, at 100, the warning flags would be reset 142 until a new warning condition was detected. The microprocessor would proceed at 146 to other program steps.

The activity subroutine 138 can be used when a sensor, such as sensor 70, is available which can detect contemporaneous patient activity levels. It is inadvisable to attempt to warn a patient if that patient is asleep or engaged in such vigorous activity or exercise that the warning is not likely to be noticed. The microprocessor 28, therefore, reads 148 the sensor 70 to determine the current level of detected activity of the patient. If the activity is too high, indicating high exercise levels or other distracting influences, the microcomputer branches at 150 to the set flag step 140. If the activity is too low, implying sleep, the microcomputer branches again at 152 to the set flag step 140. Note that this subroutine 138 is preferably not used if an emergency condition exists. Thus is a patient were about to receive a cardioverting shock, a warning would be delivered even if the patient were exercising excessively.

We will now describe the deliver warning subroutine 100 with more particularity in connection with FIG. 4. After beginning the subroutine at 102, the microprocessor would command 106 the warning stimulus generator to output an impulse at a pre-determined voltage. Alternatively, the output of another pulse generator might be switched to a warning electrode. In the illustrated embodiment, the pacemaker would then deliver a sequence of pulses through the warning stimulus generator 72 of the pacemaker. Preferably, the initial voltage level for the warning pulse would be determined on a case-by-case basis by the attending physician, in substantially the same manner in which threshold stimulus levels for the atrial and ventricular stimulus generators are determined and programmed into implantable pacemakers. In the case of the warning pulse voltage level, the physician would adjust the level of the stimulus until an appropriate response was observed or reported by the patient. Storing the voltage level setting in the microprocessor would simultaneously record the level of output of the sensor 70, to be used as a standard, as described below.

The magnitude of the output stimulus at the warning electrode is also adjusted in response to the sensed reaction of the patient. A stimulus is delivered 108 as described above. The pacemaker 10 then tests to detect 110 the resulting reaction of the patient. In the illustrated embodiment, wherein an accelerometer is used for the reaction sensor, a single, relatively short, relatively high magnitude acceleration within a preselected period of time after the delivery of the stimulus would be indicative that the patient had responded to the stimulus. The magnitude of the detected acceleration as compared with the level recorded during initial set-up, as described above, would correlate to the effectiveness of the warning, either too small, and therefore potentially imperceptible, or too large, and therefore potentially painful. The magnitude of the reaction is checked 112 and compared with the preselected level.

If the magnitude of the reaction is too low or does not occur, the stimulus is increased 114. Counter A is incremented 116. The counter A is a fail-safe counter to prevent the pacemaker 10 from becoming trapped in an endless loop, attempting futilely to produce a reaction if no reaction is detected after a pre-determined number of attempts. The counter A is tested 118 and if a pre-determined limit has been reached without detected reaction, the attempt to warn the patient is terminated 128.

If the magnitude of the reaction is too high 120, the stimulus is decreased 122. If the magnitude of the detected reaction falls above the lower boundary, counter B is incremented 124. The microprocessor then tests 126 the count B of correct stimulation pulses and either repeats the sequence described above, or terminates 128 the warning. To terminate 128 warning, the latest level of the warning stimulus voltage is stored to be used as the initial value in a subsequent warning attempt, and both counters A and B are reset to their initial values. The microprocessor then returns 130 to other programming.

Although we have described a muscle stimulation as a warning signal, other warning signals could also be used, such as an audible signal, or a nerve stimulation, or a vibration signal.

Our invention may be embodied in other specific forms without departing from the spirit or essential characteristics thereof. The present embodiment is therefore considered in all respects to be illustrative and not restrictive, the scope of our invention being indicated by the appended claims whether by the foregoing description and all changes which come within the meaning and range of equivalency of the claims are therefore intended to be embraced therein.

We claim as our invention:

1. An implantable cardiac stimulator system comprising a cardiac stimulator comprising means for producing a cardiac therapy, means for detecting a predetermined condition, means for producing a physiologic stimulation signal to warn said patient of said detected condition, and means for delaying delivery of said physiologic stimulation signal to a selected time of day, and at least one lead, said lead comprising at least one electrode adapted to be implanted adjacent a patient's heart for delivering said cardiac therapy to the heart, and a conductor for electrically connecting said therapy producing means to said electrode.

2. The implantable cardiac stimulator system according to claim 1 further comprising a sensor for detecting activity of a patient and means responsive to said sensor for inhibiting delivery of said physiologic stimulation unless said patient's activity falls in a preselected range.

3. The implantable cardiac stimulator system according to claim 1 wherein said means for delaying further comprises a real time clock.

4. The implantable cardiac stimulator system according to claim 3 wherein said means for delaying comprises means for synchronizing said real time clock with a patient's diurnal rhythms.

5. The implantable cardiac stimulator system according to claim 4 wherein said means for synchronizing comprise a sensor for detecting activity of said patient.

6. The implantable cardiac stimulator system according to claim 5 further comprising means responsive to said sensor for inhibiting delivery of said physiologic stimulation unless said patient's activity falls in a preselected range.

7. The implantable cardiac stimulator system according to claim 5 wherein said sensor is an accelerometer.

8. The implantable cardiac stimulator system according to claim 5 wherein said sensor is a microphone.

9. The implantable cardiac stimulator system according to claim 1 wherein means for delaying comprises means for detecting a pre-determined condition and means for timing a pre-selected period after detection of said condition.

10. The implantable cardiac stimulator system according to claim 9 wherein said pre-determined condition is activity indicating wakefulness.

11. The implantable cardiac stimulator system according to claim 9 wherein said means for detecting a pre-determined condition comprises means for estimating a duration of said condition.

12. The implantable cardiac stimulator system according to claim 11 wherein said pre-selected period comprises a selected fraction of said duration.

13. The implantable cardiac stimulator system according to claim 11 wherein said pre-determined condition is activity indicating wakefulness.

14. The implantable cardiac stimulator system according to claim 1 further comprising sensor means for detecting a reaction of said patient to application of said physiologic stimulation, and means for adjusting the magnitude of said physiologic stimulation in response to said sensor means.

15. The implantable cardiac stimulator system according to claim 14 further comprising means responsive to said sensor for inhibiting delivery of said physiologic stimulation unless said patient's activity falls in a preselected range.

16. The implantable cardiac stimulator system according to claim 14 wherein said sensor means is an accelerometer.

17. The implantable cardiac stimulator system according to claim 14 wherein said sensor means is a vibration sensor.

18. The implantable cardiac stimulator system according to claim 14 wherein said means for adjusting comprises means for increasing the magnitude of said physiologic stimulation until a level of reaction greater than a preselected minimum level of reaction is detected by said sensor means.

19. The implantable cardiac stimulator system according to claim 18 wherein said means for adjusting comprises means for decreasing the magnitude of said physiologic stimulation until a level of reaction less than a preselected maximum level of reaction is detected by said sensor means.

20. The implantable cardiac stimulator system according to claim 19 wherein said sensor means is an accelerometer.

21. The implantable cardiac stimulator system according to claim 19 wherein said sensor means is a vibration sensor.

22. The implantable cardiac stimulator system according to claim 14 wherein said means for adjusting comprises means for decreasing the magnitude of said physiologic stimulation until a level of reaction less than a preselected maximum level of reaction is detected by said sensor means.

23. The implantable cardiac stimulator system according to claim 1 further comprising means for distinguishing between a first set of predetermined conditions which require immediate warning to said patient and a second set of predetermined conditions which can have delayed warning to said patient and wherein said means for delaying delivery includes means responsive to said means for distinguishing for delaying warning only after detection of at least one condition from said second set of conditions.

24. An implantable medical device comprising means for producing a therapy, means for delivering said therapy to a selected portion of a patient's body, means for detecting a predetermined condition, means for producing a signal to warn said patient of said detected condition, and means for delaying delivery of said signal to a selected time of day.

25. The implantable medical device according to claim 24 wherein said means for delaying further comprises a real time clock.

26. The implantable medical device according to claim 25 wherein said means for delaying comprises means for synchronizing said real time clock with a patient's diurnal rhythms.

27. The implantable medical device according to claim 24 wherein means for delaying comprises means for detecting a pre-determined condition and means for timing a pre-selected period after detection of said condition.

28. The implantable medical device according to claim 24 further comprising means for distinguishing between a first set of predetermined conditions which require immediate warning to said patient and a second set of predetermined conditions which can have delayed warning to said patient and wherein said means for delaying delivery includes means responsive to said means for distinguishing for delaying warning only after detection of at least one condition from said second set of conditions.

* * * * *